United States Patent [19]

Ohishi et al.

[11] Patent Number: 5,468,962
[45] Date of Patent: Nov. 21, 1995

[54] INFRARED GAS ANALYZER

[75] Inventors: Mitsuru Ohishi; Wataru Nakagawa; Masahiro Uno, all of Tokyo, Japan

[73] Assignee: Fuji Electric Co., Ltd., Japan

[21] Appl. No.: 309,510

[22] Filed: Sep. 23, 1994

[30] Foreign Application Priority Data

Sep. 24, 1993 [JP] Japan .................................. 5-236999
Jun. 30, 1994 [JP] Japan .................................. 6-148808

[51] Int. Cl.⁶ .................................................. G01N 21/61
[52] U.S. Cl. .................................... 250/343; 250/345
[58] Field of Search .................................... 250/345, 343, 250/344, 346, 349

[56] References Cited

U.S. PATENT DOCUMENTS

4,772,790   9/1988   Aldridge .................................. 250/343

*Primary Examiner*—Carolyn E. Fields
*Attorney, Agent, or Firm*—Parkhurst, Wendel & Rossi

[57] ABSTRACT

An infrared gas analyzer, of compact and inexpensive design, has improved detection sensitivity. The infrared gas analyzer includes an infrared radiation source, a measuring cell, a reference cell, and a detector. The detector includes two detector cells in which the same species of gas, as the gas to be analyzed, is enclosed. A gas flow channel connects the detector cells to each other. Two thermal sensors are disposed in the gas flow channel, each of which further includes pairs of thermo-elements. The thermo-elements are arranged in such close proximity to each other, as to originate a thermal coupling between the pairing elements, and the thermo-element pairs are separated by a distance across which thermal coupling between the thermo-element pairs becomes insignificant. The detector detects, by the thermal sensors, a gas flow indicative of infrared absorption intensity difference between the measuring and reference cells.

14 Claims, 6 Drawing Sheets

INFRARED GAS ANALYZER

FIELD OF THE INVENTION

The present invention relates to an absorption type infrared gas analyzer for qualitatively or quantitatively analyzing gas species contained in a sample gas.

BACKGROUND

Figure 7:
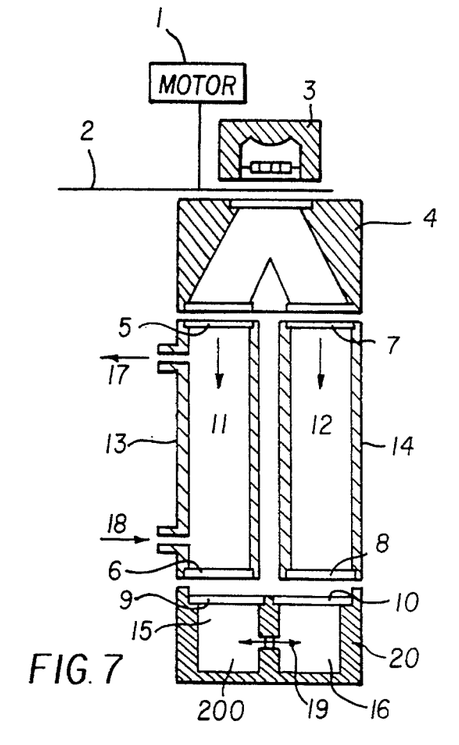
FIG. 7 is a diagram showing a main portion of the double beam infrared gas analyzer according to the prior art.

Absorption type infrared gas analyzers, which qualitatively or quantitatively analyze gas species contained in a sample gas based on infrared absorption by the gas species, are widely used in various technical fields because of their excellent selectivity and high sensitivity. The configuration and the operation principle of a conventional absorption type double beam infrared gas analyzer is explained, for example, with reference to FIG. 7. In FIG. 7, infrared radiation from an infrared radiation source 3 is chopped by a rotating chopper 2 to an infrared beam train flashing with a predetermined frequency. The beam train is divided into two beams by a distributor cell 4. One of the divided beams is led as a measuring beam 11 to a measuring cell 13 and the other divided beam is led as a reference beam 12 to a reference cell 14. The measuring cell 13 is comprised of infrared windows 5, 6 and inlet pipes 17, 18 through which a sample gas containing a component gas to be analyzed is introduced into or ejected from the measuring cell 13. The measuring beam 11 is absorbed in the measuring cell 13 depending on the content of the component gas to be analyzed.

The reference cell 14 is comprised of infrared windows 7, 8. A gas which does not absorb the infrared beam, nitrogen gas for example, is enclosed in the reference cell 14. The beams 11 and 12 which have passed through the cells 13 and 14 respectively are introduced into a gas enclosing type detector 20. The detector 20 includes the first and the second expansion cells 15 and 16 on which infrared windows 9 and 10 are respectively installed. A same species of gas with the gas to be analyzed is enclosed in the detector 20. The beam 11 impinges into the first expansion cell 15 through the infrared window 9 and the reference beam 12 impinges into the second expansion cell 16 through the infrared window 10. The detector 20 further includes a gas flow channel 19 which connects the expansion cells 15 and 16 to each other. A gas flow is originated across the channel 19 by pressure variation difference originated as a result of infrared absorption difference between the expansion cells 15, 16 corresponding to the content of the gas to be analyzed contained in the sample gas.

Figure 8A:
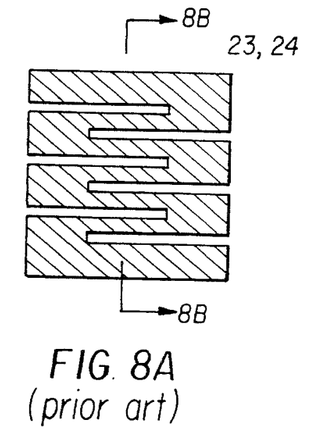
FIGS. 8(A), 8(B) and 8(C) show connections of the thermo-elements in the detector according to the prior art.

Thermo-elements 23, 24 in a thermal sensor 21 are shown in FIGS. 8(A), (B) and (C). FIG. 8(A) shows a front view of the thermo-elements 23 and 24, which are formed into two flat grids made of electrically conductive material such as metal or ceramics. The illustrated example of the thermo-element 23 or 24 is comprised of a resistor (hatched portion) fabricated by forming narrow interdigital slits by etching on a rectangular nickel foil. The thermo-elements 23 and 24 are arranged one over another with a narrow spacing in between as shown in FIG. 8(B).

Figure 8B:
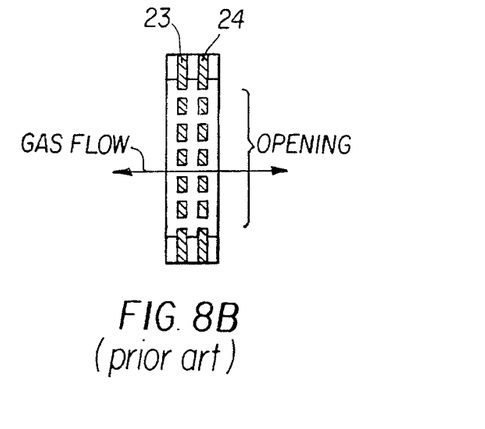
Figure 8C:
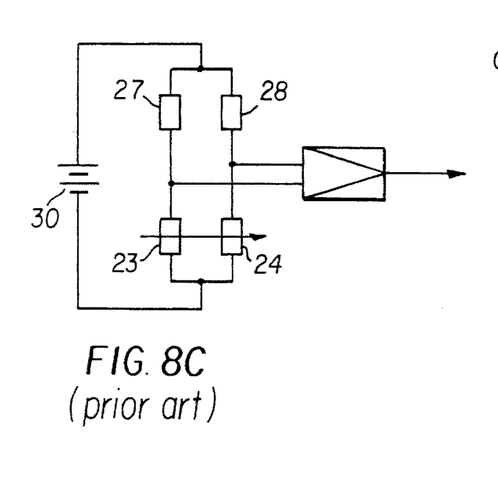

FIG. 8(B) shows a sectional view taken along A—A of FIG. 8(A) of the thermo-elements 23 and 24. The hatched portions of FIG. 8(B) show portions of the above described zigzag train of the electrically conductive foil, the resistance of which varies sharply with temperature. The thermo-element 23 is placed on the left hand side and the thermo-element 24 is positioned in close proximity to the element 23. The corresponding central portions of the thermo-elements 23, 24 are formed as an opening which is arranged perpendicularly in the channel 19 which connects the first and second expansion 15 and 16 to each other. The thermo-elements 23 and 24 are respectively connected to resistors 27 and 28 to form a Wheatstone bridge circuit. The thermo-elements 23, 24 are heated up above the room temperature by electric power supplied to the Wheatstone bridge circuit. The thermo-elements 23, 24 are positioned in such close proximity as thermal coupling occurs between the elements 23, 24.

When a gas flow occurs through the channel 19 in response to pressure difference between the first and second expansion cells 15 and 16, the gas flow varies temperature distribution around the thermo-elements 23, 24. The Wheatstone bridge circuit detects the temperature distribution variation as an indication of the pressure difference.

The prior art infrared gas analyzer comprised of the Wheatstone bridge circuit consisting of two thermo-elements and two resistors is not sensitive enough to analyze low concentration gas species since the Wheatstone bridge circuit utilizes only the resistance change of the two thermo-elements. The infrared gas analyzer according to the prior art has solved this problem with an elongated measuring cell or with an infrared radiation source of high radiance. However, the elongated cell hinders down sizing of the optical system, and the high radiance radiation source requires additional thermal means, including a radiator, since the high radiance radiation source is realized by a high source temperature, which increases the size and cost of the infrared gas analyzer.

In view of the foregoing, an object of the present invention is to provide an infrared gas analyzer with improved sensitivity, small size and low cost which facilitates stable measurement of a gas of low content.

SUMMARY OF THE INVENTION

The object of the present invention is achieved by an infrared gas analyzer which includes an infrared radiation source, a measuring cell, into which a gas to be analyzed is introduced and in which an infrared beam fed from the radiation source is absorbed by the gas to be analyzed, and a detecting means that includes an enclosed gas with the same absorption wavelength range with the gas to be analyzed, two detector cells, a gas flow channel connecting the detector cells to each other, and a plurality of thermal sensors, disposed in the gas flow channel, for detecting a gas flow in the gas flow channel and for converting the detected gas flow to an electric signal, wherein each of the thermal sensors further includes a pair of thermo-elements.

The pair of thermo-elements are preferably located adjacent to each other closely enough to form a temperature field by thermal coupling between the pairing thermo-elements, and the thermal sensors are separated by a distance sufficient to insure negligible thermal coupling therebetween.

The plurality of thermal sensors preferably include two pairs of thermal sensors, the thermo-elements of which located on the upstream side of the gas flow are connected onto a pair of opposed sides of a Wheatstone bridge, and the thermo-elements of which located on the downstream side of the gas flow are connected onto another pair of opposed sides of the Wheatstone bridge.

It is preferable that a plurality of thermo-elements located on the upstream side of the gas flow are connected into a series circuit, a plurality of thermo-elements located on the downstream side of the gas flow are connected in another series circuit, and each of the series circuits is connected to a fixed resistor to form a Wheatstone bridge.

It is also preferable that a plurality of thermo-elements located on the upstream side of the gas flow are connected into a series circuit, a plurality of thermo-elements located on the downstream side of the gas flow are connected in another series circuit, and each of the series circuits is driven by a constant current supply.

The intensity difference of the infrared beams which impinge into the detector cells is converted into pressure difference between the detector cells, which originates a gas flow flowing through the channel which connects the detector cells to each other. The gas flow flows alongside the pairing thermo-elements or through an opening of the pairing thermo-elements of a plurality of the thermal sensors disposed in the gas flow channel. The thermo-elements are connected in a bridge circuit or driven by a constant current. Each pair of the thermo-elements is self-heated by a current flowing through the elements themselves to form around the each pair a temperature field higher than the gas environment in the gas flow channel. The thermal sensors, each of which is comprised of a pair of thermo-elements, are separated by a distance across which thermal coupling between the sensors can be ignored.

In the infrared gas analyzer with the above configuration, the pairing thermo-elements are heated by a power supply for the bridge circuit. The heat from the thermo-elements arranged in close proximity to each other heats up the gas around the thermo-element pair. A weak gas flow originated in the gas flow channel by the pressure difference between two detector cells shifts the temperature field around the thermo-element pair. The shift of the temperature field or variation of temperature distribution varies resistance values of the thermo-elements. Thus, the infrared absorption in the cell which represents concentration of the gas to be analyzed is measured by detecting with the bridge circuit variation of the resistance values or variation of the temperature distribution.

A detector circuit is comprised of four thermo-elements, two of which constitute a thermal sensor, arranged on a side of a Wheatstone bridge one by one in a configuration that the upstream side element of one of the thermo-element pairs and the downstream side element of another pair are connected onto opposed sides, and the downstream side element of one of the thermo-element pairs and upstream side element of another pair are connected onto the other opposed sides of the Wheatstone bridge circuit. The Wheatstone bridge circuit thus constructed compensates increment and decrement of the series resistance values of the thermo-elements connected to a power supply for the bridge circuit, and maintains the currents which flow through the thermo-elements at an almost constants value. Therefore, the Wheatstone bridge circuit stably operates at a relatively low bridge power supply voltage in a state that the thermo-elements, the resistance of which sharply changes with temperature, are self-heated.

The infrared gas analyzer includes a plurality of thermal sensors, the upstream side thermo-elements of which are connected in series and the downstream side elements are connected in series respectively, multiplies its detection signal voltage by the numbers of the thermal sensors incorporated, by constructing a bridge circuit with the two series circuits and two fixed resistors either one of which is connected to either one of the series circuit, by increasing the bridge power supply voltage, and by adjusting the currents flowing through the bridge sides at the same value.

The series upstream side elements circuit and the series downstream side elements circuit may be separately driven by two constant current power supplies. By constructing constant current supplies with operational amplifiers, this configuration, which corresponds to the above described bridge circuit with its resistors of infinite resistance, facilitates lowering bridge power supply voltage in comparison with the bridge circuit with the resistors of infinite resistance, driving the thermo-elements by a constant current, and increasing detection sensitivity by the numbers of the thermal sensors.

Temperature dependence of the sensitivity of the thermo-element is compensated by controlling the current flowing through the thermo-element by the output of the temperature sensor incorporated into the infrared gas analyzer. Variation of the infrared absorption caused by pressure variation (density variation) in the measuring cell is compensated by controlling the current flowing through the thermo-element by the output of the pressure sensor incorporated into the measuring cell.

Other advantages and feature of the invention will become apparent from the detailed description of the preferred embodiments of the invention presented below.

BRIEF DESCRIPTION OF THE DRAWINGS

The invention will be described in greater detail with reference to certain preferred embodiments thereof and the accompanying figures, wherein.

DETAILED DESCRIPTION OF THE PREFERRED EMBODIMENTS

Figure 1A:
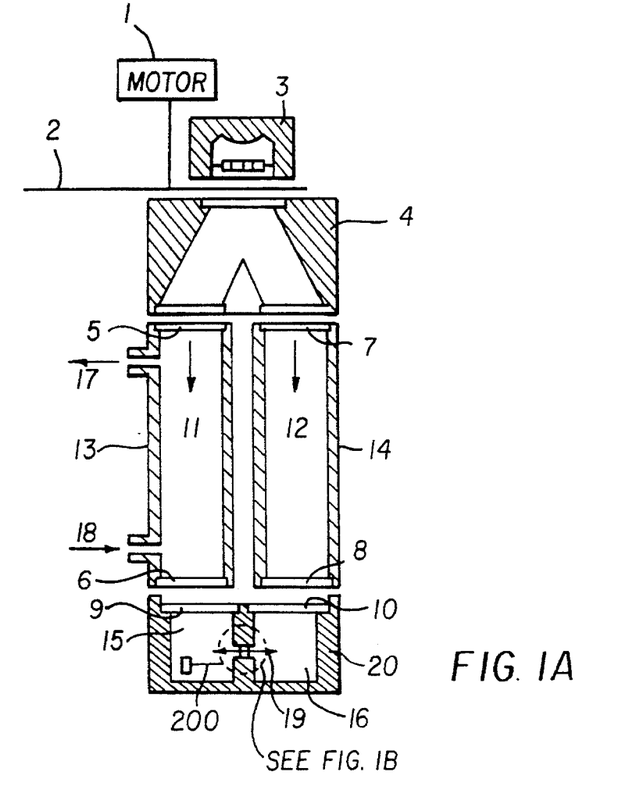
FIG. 1 is a diagram showing a main portion of an embodiment of a double beam infrared gas analyzer according to the present invention.
Figure 1B:
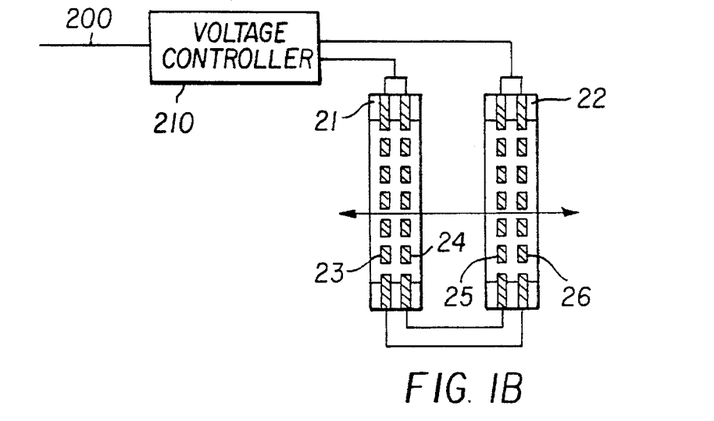

FIG. 1 is a diagram showing a main portion of an embodiment of a double beam infrared gas analyzer according to the present invention. In FIG. 1, an infrared ray emitted from an infrared radiation source 3 is chopped by a rotating chopper 2 to a flashing beam train. The beam train is then divided into two beams by a distributor cell 4. One of the divided beams is led as a measuring beam 11 to a measuring cell 13. The other divided beam is led as a reference beam 12 to a reference cell 14. Infrared windows 5, 6 are installed on a measuring cell 13, into which a sample gas which contains gas species to be analyzed is introduced through an inlet pipe 18. The sample gas is ejected through an exit pipe 17 from the measuring cell 13. The measuring beam 11 is absorbed in accordance with the concentration the gas species to be analyzed in the measuring cell 13.

The reference cell 14, on which infrared windows 7, 8 are installed, contains a gas which does not absorb the infrared ray. The measuring beam 11 which has passed through the measuring cell 13 and the reference beam 12 which has passed through the reference cell 14 are fed to a detector 20. The detector 20 includes first and second detector cells (hereinafter referred to as the first and second expansion cells) 15 and 16, on which infrared windows 9 and 10 are installed respectively. The expansion cells 15, 16 are filled with the same species of gas with the gas to be analyzed. The measuring beam 11 impinges into the first expansion cell 15 through the window 9, and the reference beam 12 impinges into the second expansion cell 16 through the window 10.

Figure 3A:
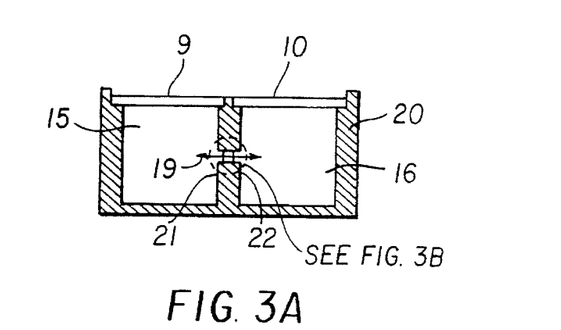
FIGS. 3(A) and 3(B) show diagrams for explaining the detector of FIG. 1.
Figure 3B:
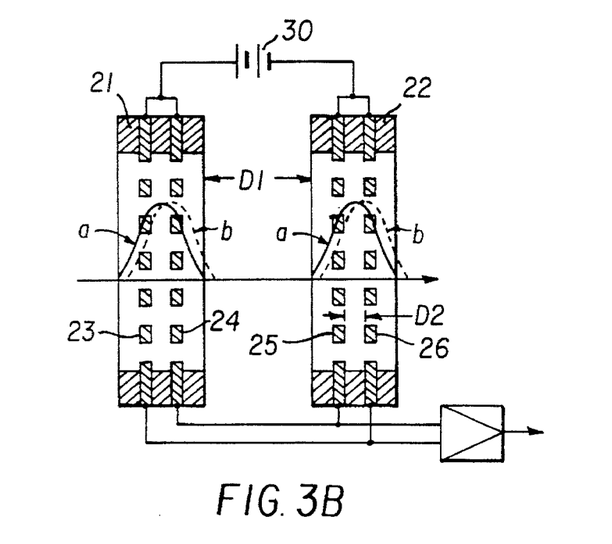

Now an example of the detector 20 is explained with reference to FIGS. 3(A) and (B). In FIG. 3 (A), the detector 20 is comprised of first and second expansion cells 15, 16 and a gas flow channel 19 which connects the expansion cells 15 and 16 to each other. A plurality of thermal sensors (two sensors 21, 22 in the illustrated embodiment), each of which is further comprised of a pair of thermo-elements 23, 24 or 25, 26, are installed on a portion A of the gas flow channel 19. The thermo-elements can be made from an electrically conductive metal, ceramics, or a semiconductor. The infrared beams 11 and 12, which have impinged into the expansion cells 15 and 16, respectively originate a pressure variation difference between the cells 15 and 16 depending on infrared absorption difference between the cells 15 and 16. As a result of the originated pressure variation difference, a gas flow occurs through the gas flow channel 19 corresponding to the content of the gas to be analyzed in the sample gas. FIG. 3(B) shows a detail structure of the thermal sensors 21, 22. In FIG. 3 (B), thermal sensors 21, 22, which were explained with reference to FIGS. 8(A) and (B), are arranged with a separation distance D1, preferably not less than 1000 µm, is sufficient to insure negligible thermal coupling between the thermal sensors. The thermo-elements of each pair (23, 24) (25, 26) are preferably 5 mm×5 mm in dimension and are located adjacent to each other within a distance D2 of between 100–300 µm. Assuming that the enclosed gas flows from the left hand side (upstream side) to the right hand side (downstream side) as a straight arrow in FIG. 3(B) shows, the upstream side thermo-elements 23, 25 are connected onto one of the opposed sides pairs of a Wheatstone bridge and the downstream side thermo-elements 24, 26 are connected onto another pair of opposed sides of the Wheatstone bridge. As shown in the figure, the thermo-elements 23, 24 belong to the thermal sensor 21 and the elements 26, 26 belong to the other thermal sensor 22.

When the enclosed gas does not flow, the thermo-elements 23, 24, 25, 26 are heated up (preferably to about 150 degrees Centigrade) by a current supplied from a bridge power supply 30, as a result of which a temperature distribution indicated by a solid curve a in FIG. 3(B) is originated around each thermo-element pair (23, 24), (25, 26) by thermal coupling between the paired thermo-elements (23, 24), (25, 26). As was stated above, the thermal sensors 21, 22 are separated from each other by a distance over which mutual thermal coupling can be ignored. When a weak gas flow occurs in the gas flow channel 19, the gas flows through the thermally coupling thermo-elements to shift the temperature distribution to a temperature distribution indicated by a broken line b in FIG. 3(B). In the figure, the temperature around the thermo-elements 23, 25 lowers and the temperature around the thermo-elements 24, 26 rises. In response to this temperature variation, resistance of each thermo-element changes sharply. The weak gas flow is detected by amplifying a signal from the Wheatstone bridge, the unbalance of which is originated by the above described resistance change of the thermo-elements.

Figure 4A:
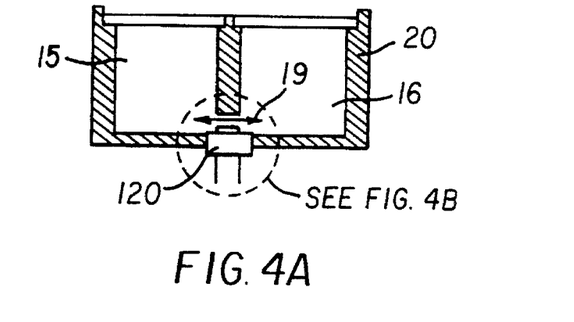
FIGS. 4(A), 4(B) and 4(C) show diagrams of another embodiment of the detector.
Figure 4B:
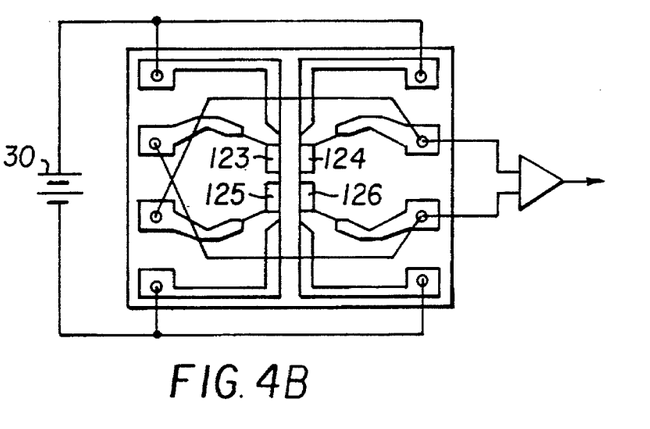
Figure 4C:
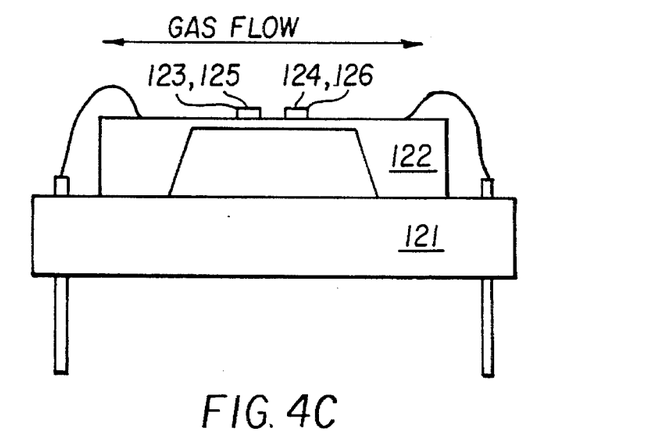

FIGS. 4(A), (B) and (C) show another embodiment of the detector. In FIG. 4(A), the detector 20 is comprised of the first expansion cell 15, the second expansion cell 16 and the gas flow channel 19. A detector module 120, comprised of two pairs of thermo-elements (123, 124) and (125, 126), is installed on a portion B of the gas flow channel 19. The infrared beams 11 and 12 which have impinged into the expansion cells 15 and 16 respectively originate pressure variation difference between the cells 15 and 16 depending on infrared absorption difference between the cells 15 and 16. As a result of the produced pressure variation difference, a gas flow occurs through the gas flow channel 19 corresponding to the content of the gas to be analyzed in the sample gas. FIGS. 4(B) and (C) show a configuration of the detector module 120 in detail. FIGS. 4(B) is a top plan view and FIG. 4(C) is a side plan view of the detector module 120. As FIG. 4(B) shows, the detector module 120 is comprised of two thermal sensors, each of which is further comprised of a pair of thermo-elements (123,124) or (125, 126), mounted on a substrate. In the illustrated embodiment, thin-film thermo-elements from 123 to 126 are formed by the conventional thin-film formation techniques on a silicon substrate 122. A bottom portion of the silicon substrate 122 is etched off, as shown in FIG. 4(C), to reduce heat capacity and to prevent heat dissipation by conduction. The silicon substrate 122 is fixed to a base 121. In the detector module 120, the upstream side thermo-elements 123,125 are connected onto one of the opposed side pairs of a Wheatstone bridge and the downstream side thermo-elements 124, 126 are connected onto another pair of opposed sides of the Wheatstone bridge in a similar connection as that shown in FIG. 3(B). The thermo-elements from 123 to 126 are heated up by a current supplied from the bridge power supply 30 and locally elevated temperature distribution is originated. When a weak gas flow occurs in the gas flow channel 19, the gas flows over the thermo-elements, by which resistance of each thermo-element is changed sharply. The weak gas flow, as an indication of pressure difference between the expansion cells of the detector, is detected by amplifying an unbalance signal from the Wheatstone bridge circuit, the unbalance of which is originated the above described resistance change of the thermo-elements.

Figure 5A:
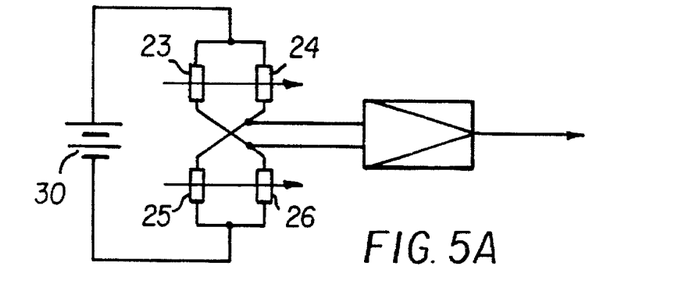
FIGS. 5(A), 5(B) and 5(C) show circuit diagrams for explaining the configuration of the bridge circuits.
Figure 5B:
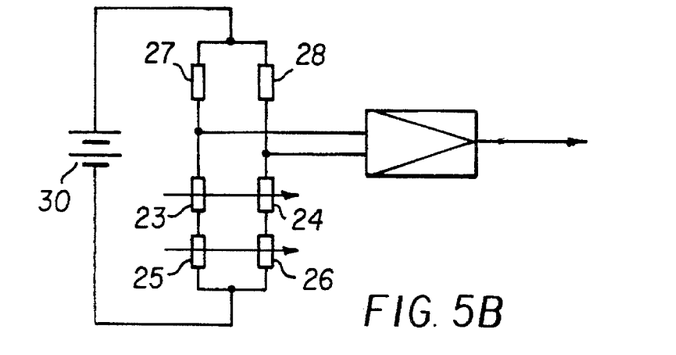
Figure 5C:
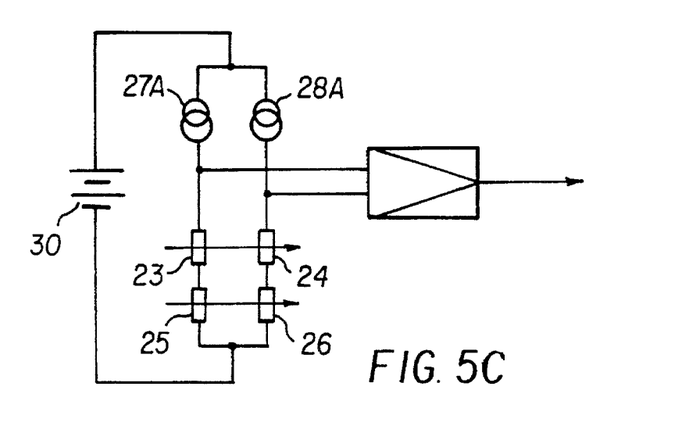

FIGS. 5(A)–(C) show circuit diagrams for explaining the bridge circuit configuration examples. The detector circuit of FIG. 5(A), is constructed by connecting the upstream side thermo-elements 23, 25 onto one of the opposed side pairs of a Wheatstone bridge and downstream side thermo-elements 24, 26 onto another pair of opposed sides of the Wheatstone bridge. Electric power is supplied from the bridge power supply 30. The Wheatstone bridge circuit thus constructed compensates for increments and decrements of the series resistance values of the thermo-elements (23, 26) and (24, 25) connected in series to the power supply for the bridge circuit, and maintains the currents which flow through the thermo-elements at an almost constant values. Therefore, this Wheatstone bridge circuit stably operates at relatively low bridge power supply voltage in a state that the thermo-elements, the resistance of which sharply changes with temperature, are self-heated. The voltage applied to the thermo-elements 123 to 126 is sufficient for heating the thermo-elements up to a temperature that is one order of magnitude higher then the room temperature.

The detector circuit of FIG. 5(B) connects the upstream side thermo-elements 23, 25 in a series circuit and the downstream side elements 24, 26 in another series circuit. The detector circuit multiplies detection signal voltage by the number of the thermal sensors (thermo-element pairs) incorporated, by constructing a bridge circuit with the above described series circuits and two fixed resistors 27, 28, either one of which is connected to either one of the series circuit, by increasing the bridge power supply voltage, and by adjusting the currents flowing through the bridge sides at the same value. Resistance of the fixed resistors 27, 28 are set at a value one order of magnitude higher than the resistance value of the series circuit, for guaranteeing detection voltage sensitivity and for maintaining current supply to the bridge circuit as constant as possible, which requires relatively high voltage of the power supply 30.

The detector circuit of FIG. 5(C) connects the upstream side thermo-elements 23, 25 in a series circuit and the downstream side elements 24, 26 in another series circuit. These series circuits are driven by two constant current supplies 27A, 27B, and voltage drop difference between across the series circuits is amplified to obtain a detection signal. This configuration is equivalent to the detection circuit of FIG. 5(B), the resistance of the resistors 27, 28 of which is infinite. By constructing constant current supplies with operational amplifiers, this configuration facilitates lowering bridge power supply voltage by about 10 V in comparison with the bridge circuit of FIG. 5(B), driving the thermo-elements by a constant current, and increasing detection sensitivity by the numbers of the incorporated thermal sensors (thermo-element pairs).

Figure 2A:
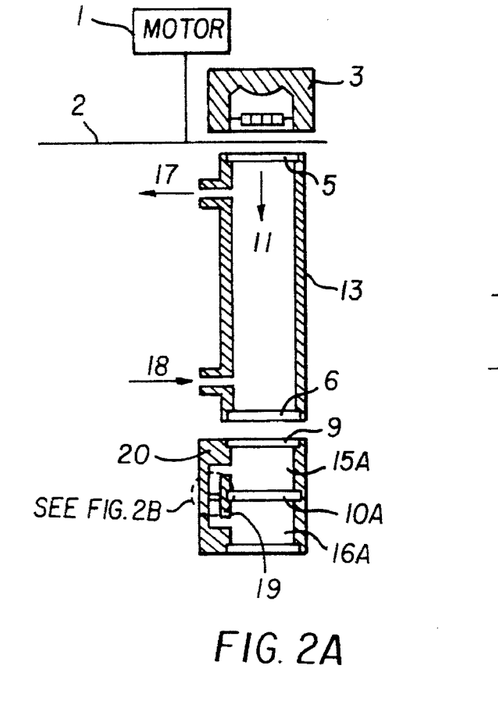
FIG. 2 is a diagram showing a main portion of an embodiment of a single beam infrared gas analyzer according to the present invention.
Figure 2B:
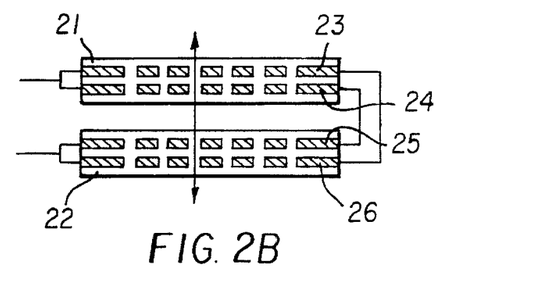

FIG. 2 is a diagram showing a main portion of an embodiment of a single beam infrared gas analyzer according to the present invention. In FIG. 2, an infrared ray emitted from an infrared radiation source 3 is chopped by a rotating chopper 2 to a flashing beam train, The beam train impinges as a measuring beam 11 into a measuring cell 13. The measuring cell 13 is comprised of an infrared windows 5, 6, and inlet and exit pipes 17, 18 through which a sample gas containing a gas spices to be analyzed is introduced into or ejected from the measuring cell 13. The measuring beam 11 is absorbed in the measuring cell 13 according to the content of the gas to be analyzed. The unabsorbed measuring beam 11 impinges into a detector 20.

The detector 20 is comprised of the first expansion cell 15A and the second expansion cell 16A aligned along the propagation direction of the beam 11. The measuring beam 11 which has passed through the measuring cell 13 impinges into the first expansion cell 15A through a window 9 and the measuring beam 11 which has passed through the first expansion cell 15A impinges into the second expansion cell 16A through a window 10. The same species of gas with the gas to be analyzed is filled in the expansion cells 15A, 16A. In the first expansion cell 15A as a front cell, most part of the infrared beam of wavelength range in which the gas species to be analyzed shows a high absorption coefficient is absorbed. The remaining measuring beam 11 which has not been absorbed in the expansion cell 15A impinges into the second expansion cell 16A. In the second expansion cell 16A, the remaining measuring beam 11 of wavelength range in which the gas species to be analyzed shows an intermediate absorption coefficient is absorbed. A gas flow is originated in the gas flow channel 19 by absorbed infrared intensity difference between the expansion cells 15A and 16A. A plurality of thermal sensors (two sensors 21, 22 in the illustrated example), each of which is further comprised of a pair of thermo-elements 23, 24 (25, 26), are installed on a portion A of the gas flow channel 19. In contrast to the embodiment of FIG. 1, in which the gas flow channel 19 is arranged horizontally, the gas flow channel 19 is arranged vertically in the embodiment of FIG. 2. Though the enclosed gas flows vertically in the embodiment of FIG. 2, the detection principle by the plurality of thermal sensors is not different from that for the embodiment of FIG. 1.

In FIG. 1, a temperature sensor 200 is disposed in the detector 20 for measuring the temperature in the detector 20. A voltage controller 210 controls, for obtaining a stably operating infrared gas analyzer, the thermo-elements from 23 to 26 or the thin-film thermo-elements from 123 to 126 at an appropriate operation temperature to compensate for temperature dependence of the thermo-elements which usually increases gain with elevated temperature. The temperature sensor 200 may be positioned anywhere in the infrared gas analyzer in which the temperature in the vicinity of the detector 20 can be measured.

Figure 6A:
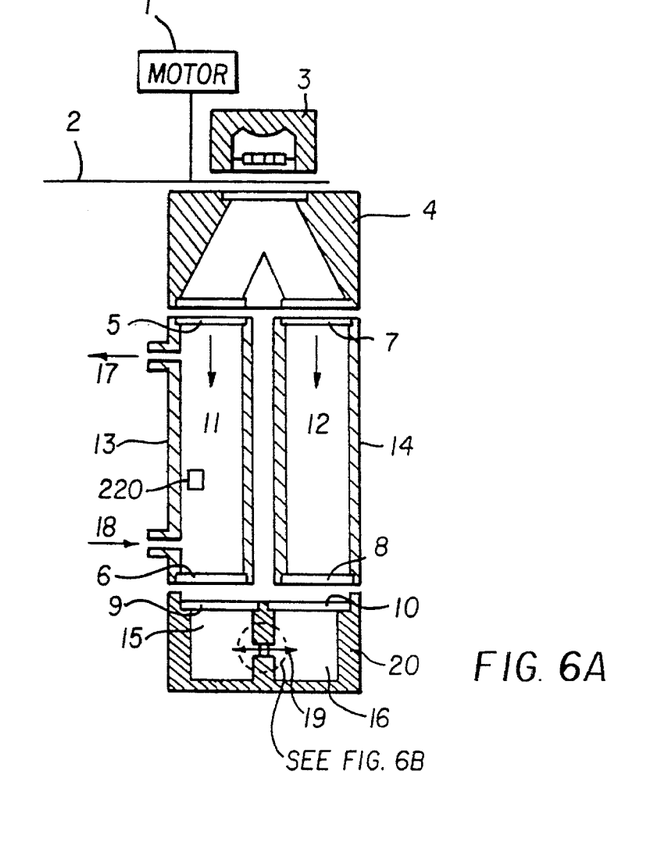
FIG. 6 is a diagram showing a configuration of a double beam infrared gas analyzer into which a compensation function with a pressure sensor is incorporated.
Figure 6B:
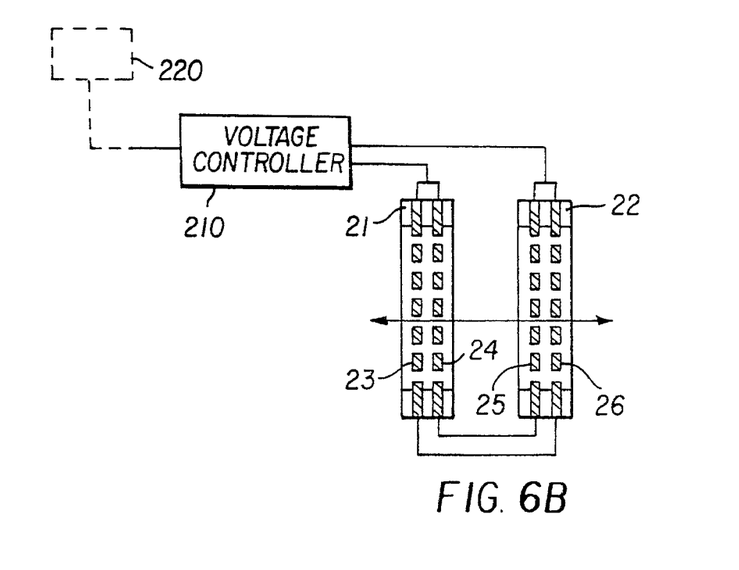

FIG. 6 shows an embodiment which compensates variation of the sensitivity of the analyzer associated with atmospheric pressure variation with a pressure sensor 220 disposed in the measuring cell 13. According to the prior art, detector output is subject to an error caused by density variation of the gas to be measured associated with atmospheric pressure variation since one end of the measuring cell of the infrared gas analyzer is usually open to the atmosphere. The sensitivity of the infrared gas analyzer is compensated by detecting pressure in the measuring cell 13 with the pressure sensor 220 and by controlling the temperature of the thermo-elements from 23 to 26 or that of the thin-film thermo-elements from 123 to 126 at an appropriate operation temperature by the voltage controller 210. When the output of the detector 20 lowers, for example, in association with lowering of the internal pressure of the measuring cell 13, the voltage controller increases its output to rise the operation temperature of the thermo-elements from 23 to 26 or that of the thin-film thermo-elements from 123 to 126 for increasing detection output of the detector 20 and for compensating variation of the measured value caused by the internal pressure variation of the measuring cell.

The thermo-elements from 23 to 26 of FIGS. 1, 2 and 6 may be replaced by the detector module 120 into which the thin-film thermo-elements from 123 to 126 are integrated. The full bridge circuit connection of FIG. 5(A) used in FIGS. 1, 2 and 6 may be replaced by the half bridge circuit connection of FIG. 5(B) or by the bridge circuit driven at a constant current of FIG. 5(C).

As explained above, the infrared gas analyzer according to the present invention detects a pressure difference between two detector cells by a pair of thermal sensors, each of which is comprised of a pair of thermo-elements, which are disposed in a gas flow channel connecting the detector cells to each other, and alongside or through which a gas flow originated by the pressure difference flows.

Each pair of the thermo-elements, connected into a bridge circuit and self-heated by a current supplied from a power supply for the bridge circuit, forms a temperature distribution higher than that around each pair by thermal coupling between the pairing thermo-elements. The thermo-element pairs are separated by a distance over which thermal coupling can be ignored.

The high temperature distribution around the thermo-element pairs is shifted by a weak gas flow in the gas flow channel. The shift of the temperature distribution is detected by the above described configuration as a variation of resistance of the thermo-elements.

By constructing the detector with a full bridge circuit, the currents flowing through the thermo-elements are kept at a constant value irrespective of temperature distribution variation, by which the bridge circuit is stably driven at relatively low voltage in a state in which thermo-elements are self-heated.

By constructing the detector by a half-bridge circuit, which connects upstream side and downstream side series circuit of the thermo-elements to two fixed resistors and by driving the series circuits with two constant current supplies, detection voltage of the detector can be multiplied by the numbers of the thermal sensors (thermo-element pairs) of the detector. Especially, a configuration, which replaces the two resistors by operational amplifiers and which drives the series circuits by two constant current supplies, provides a bridge circuit equivalent to the half-bridge circuit, the resistance values of the two resistors of which are infinite. This configuration is effective to lower the power supply voltage for the bridge in comparison with the half-bridge circuit with fixed resistors.

The detector is applicable to a double beam infrared gas analyzer by aligning the two detector cells perpendicularly to the propagation direction of the infrared beams. And the detector is applicable also to the single beam infrared gas analyzer by aligning the two detector cells along the propagation direction of the measuring infrared beam.

By controlling currents flowing through the thermo-elements based on the output from a temperature sensor, temperature dependence of the sensitivity of the thermo-elements can be compensated.

By controlling currents flowing through the thermo-elements based on the output from a pressure sensor, pressure dependence of the sensitivity of the thermo-elements can be compensated.

As described above, the present invention is quite effective in improving detection sensitivity of the infrared gas analyzer and providing, at low cost, an infrared gas analyzer having a small size that can stably measure a concentration of a gas to be analyzed.

The invention has been described with reference to certain preferred embodiments thereof. It will be understood, however, that modifications and variations are possible within the scope of the appended claims.

What is claimed is:

1. An infrared gas analyzer comprising:
   an infrared radiation source; a measuring cell, into which a gas to be analyzed is introduced and in which an infrared beam fed from said radiation source is absorbed by said gas to be analyzed; and a detecting means;
   wherein said detecting means includes two detector cells including gas enclosed therein having the same absorption wavelength range with said gas to be analyzed, a gas flow channel connecting said detector cells to each other, and a plurality of thermal sensors; and
   wherein each thermal sensor includes a pair of thermo-elements, disposed in said gas flow channel, for detecting a gas flow in said gas flow channel and converting the detected gas flow to an electric signal.

2. The infrared gas analyzer as claimed in claim 1, wherein said pair of thermo-elements are located adjacent to each other by a distance close enough to form a temperature field by thermal coupling between said pair of thermo-elements, and said thermal sensors are separated by a distance sufficient to insure negligible thermal coupling therebetween.

3. The infrared gas analyzer as claimed in claim 2, wherein the distance between the thermo-elements is between 100–300 μm and the distance between the thermal sensors is at least 1000 μm.

4. The infrared gas analyzer as claimed in claim 1, wherein said plurality of thermal sensors include at least two pairs of thermal sensors, first thermo-elements thereof being located on an upstream side of said gas flow are connected onto a pair of opposed sides of a Wheatstone bridge circuit and second thermo-elements thereof being located on a downstream side of said gas flow are connected onto another pair of opposed sides of said Wheatstone bridge circuit.

5. The infrared gas analyzer as claimed in claim 1, wherein a plurality of the thermo-elements are located on an upstream side of said gas flow and are connected in a series circuit, a plurality of the thermo-elements are located on a downstream side of said gas flow and are connected in another series circuit, and each of said series circuits is connected to a fixed resistor to form a Wheatstone bridge.

6. The infrared gas analyzer as claimed in claim 1, wherein a plurality of the thermo-elements are located on an upstream side of said gas flow and are connected in a series circuit, a plurality of the thermo-elements are located on a downstream side of said gas flow and are connected in another series circuit, and each of said series circuits is driven by a constant current supply.

7. The infrared gas analyzer as claimed in claim 1, wherein said thermo-elements are heated by currents flowing through said thermo-elements.

8. The infrared gas analyzer as claimed in claim 1, wherein said enclosed gas flows alongside said thermo-elements.

9. The infrared gas analyzer as claimed in claim 1, wherein said enclosed gas flows through said thermo-elements.

10. The infrared gas analyzer as claimed in claim 1, wherein said thermo-elements comprise a material selected from a group consisting of electrically conductive metal, ceramics and semiconductor, wherein the resistance of the material shows temperature dependence.

11. The infrared gas analyzer as claimed in claim 1, wherein said two detector cells are aligned along a propagation direction of said infrared beam.

12. The infrared gas analyzer as claimed in claim 1, wherein said two detector cells are aligned perpendicularly to a propagation direction of said infrared beam.

13. The infrared gas analyzer as claimed in claim 1, comprising means for adjusting currents flowing through said thermo-elements in response to an output from a temperature sensor disposed in said infrared gas analyzer.

14. The infrared gas analyzer as claimed in claim 1, comprising means for adjusting currents flowing through said thermo-elements in response to an output from a pressure sensor for measuring pressure in said measuring cell.

* * * * *